United States Patent
Blumm

(10) Patent No.: US 9,689,818 B2
(45) Date of Patent: Jun. 27, 2017

(54) THERMAL ANALYSIS DEVICE AND METHOD FOR THERMAL ANALYSIS COMPRISING GAS ANALYSIS

(71) Applicant: Netzsch-Gerätebau GmbH, Selb (DE)

(72) Inventor: Juergen Blumm, Selb (DE)

(73) Assignee: Netzsch-Gerätebau GmbH, Selb (DE)

( * ) Notice: Subject to any disclaimer, the term of this patent is extended or adjusted under 35 U.S.C. 154(b) by 691 days.

(21) Appl. No.: 13/945,692

(22) Filed: Jul. 18, 2013

(65) Prior Publication Data

US 2013/0298639 A1 Nov. 14, 2013

Related U.S. Application Data

(63) Continuation of application No. PCT/DE2011/000045, filed on Jan. 18, 2011.

(51) Int. Cl.
| | |
|---|---|
| G01N 25/00 | (2006.01) |
| G01N 25/48 | (2006.01) |
| H01J 49/04 | (2006.01) |
| G01N 5/04 | (2006.01) |
| G01N 30/72 | (2006.01) |

(52) U.S. Cl.
CPC ......... *G01N 25/00* (2013.01); *G01N 25/4846* (2013.01); *H01J 49/0459* (2013.01); *G01N 5/04* (2013.01); *G01N 30/7206* (2013.01)

(58) Field of Classification Search
None
See application file for complete search history.

(56) References Cited

U.S. PATENT DOCUMENTS

| | | | |
|---|---|---|---|
| 3,344,654 A | 10/1967 | Erdey et al. | |
| 5,442,949 A * | 8/1995 | Kinoshita | G01N 30/12 |
| | | | 422/68.1 |

(Continued)

FOREIGN PATENT DOCUMENTS

DE 3226803 A1 1/1984

OTHER PUBLICATIONS

P.A. Barnes, et al.; "High-Performance Evolved Gas Analysis System for Catalyst Characterization"; Analytical Chemistry; Jul. 1, 1994; 6 pages.

(Continued)

*Primary Examiner* — Paul West
(74) *Attorney, Agent, or Firm* — Whitmyer IP Group LLC

(57) ABSTRACT

A thermoanalysis device, including a controllable temperature regulating device for the controlled change in the temperature of a sample to be investigated, a detection device for the continuous detection of at least one signal characteristic of a property of the sample during the change in the temperature, and a gas analysis device for investigating gases which are liberated from the sample. In order to enable an improved time- and temperature-resolved investigation of volatile components and decomposition products, provision is made according to the invention such that, during the change in the temperature of the sample, the temperature regulating device is controlled according to a control algorithm taking account of the detected signal and/or the gas analysis device is constituted so as to be controllable and is controlled according to a control algorithm taking account of the detected signal.

11 Claims, 2 Drawing Sheets

(56) References Cited

U.S. PATENT DOCUMENTS

| | | | |
|---|---|---|---|
| 6,904,784 B2* | 6/2005 | Allington et al. | 73/23.35 |
| 7,140,231 B2* | 11/2006 | Arii et al. | 73/23.37 |
| 2003/0071629 A1* | 4/2003 | Yang et al. | 324/464 |
| 2005/0112027 A1* | 5/2005 | Arii | H01J 49/04 422/80 |

OTHER PUBLICATIONS

International Search Report Application No. PCT/DE2011/000045 Completed: Aug. 16, 2011; Mailing Date: Aug. 22, 2011 2 pages.

* cited by examiner

THERMAL ANALYSIS DEVICE AND METHOD FOR THERMAL ANALYSIS COMPRISING GAS ANALYSIS

FIELD OF THE INVENTION

The present invention relates to a themoanalysis device according to the preamble of claim 1 and a thermoanalysis method according to the preamble of claim 10.

BACKGROUND OF THE INVENTION

Devices and methods for "thermoanalysis" are known from the prior art and have now become established worldwide, in particular for purposes of material characterisation. Polymers, pharmaceutical substances, textiles, metals, ceramics and other organic or inorganic materials, for example, can thus be analysed and characterised.

In "thermoanalysis" (or "thermal analysis"), a sample to be investigated is subjected by means of a temperature regulating device (e.g. electrical heating device) to a controlled temperature change, e.g. a presettable "temperature program". The sample may be heated, cooled or held at a constant temperature.

Complying as precisely as possible with the temperature program usually requires that the sample temperature is continuously detected, for example measured with a temperature measuring sensor, so that a detection or measurement signal representative of the sample temperature can be used for a control (e.g. PID control) of the sample temperature.

Moreover, during the controlled change in the sample temperature, at least one (further) signal characteristic of a (further) property of the sample is continuously detected and recorded together with the course of the sample temperature.

Thermoanalysis thus enables the investigation and characterisation of temperature-related changes in properties of a sample material, including processes triggered thermally in the sample.

It is understood that the term "continuously" used here in connection with a detection (e.g. measurement) of signals also includes a quasi-continuous detection, for example one taking place at relatively small time intervals (e.g. periodically).

Thermoanalytical methods can be specified more precisely depending on which further signal or which further signals (apart from the sample temperature) are detected during the controlled change in the sample temperature. Such special methods of thermoanalysis are also known from the prior art and do not therefore require further explanation here. The following methods are mentioned solely by way of example: differential thermoanalysis (DTA), differential calorimetry (DSC) or dynamic differential calorimetry (DDK), thermogravimetry (TG) or thermogravimetric analysis (TGA) and thermomechanical analysis (TMA).

TG or a "simultaneous thermal analysis" (STA), i.e. a combination of TG and DSC or DDK, is often used for the characterisation of thermal vaporisation and decomposition effects. In a further development, apart from the detection of a loss of mass of the sample, an investigation of gases that are liberated by the sample can for example also take place. For the gas investigation, use can be made for example of Fourier transform infrared spectrometry (FTIR) or mass spectrometry (MS, for example using a quadrupole mass spectrometer).

These known methods certainly offer the possibility of analysing volatile sample components and decomposition products. However, these methods come up against their limitations in practice when, over the temporal course of the thermal analysis, several or even many different components or decomposition products are liberated and a "time- or temperature-resolved" gas analysis process that is as good as possible is intended to be obtained.

Of concern here is the fact that the investigation of gases with the known gas analysis devices, depending on their accuracy, is relatively time-consuming—measured against the time typically provided for the course of a thermoanalysis or with regard to the temperature change rates typically provided in a temperature program (in the region of approx. 1 K/min to 50 K/min).

A more accurate investigation of thermally triggered gas liberation processes, in particular a more accurate characterisation of the gas composition when many different gases are liberated simultaneously, has therefore failed hitherto.

SUMMARY OF THE INVENTION

Against this background, it is a problem of the present invention to improve a device and a method of the type mentioned at the outset, in such a way that an improved time- and temperature-resolved investigation of volatile components and decomposition products is enabled and a separation of the various gases for the actual gas analysis is produced.

According to the invention, this problem is solved by a device according to claim 1 and a method according to claim 10. The dependent claims relate to advantageous developments of the device according to the invention, wherein these developments, individually or in a combination, can also be provided in a similar way for the method according to the invention.

The basic idea of the invention consists in providing a special "functional coupling" between the temperature regulation of the sample to be investigated on the one hand and the investigation of liberated gases on the other hand.

According to the invention, during the change in the temperature of the sample its temperature regulation is controlled according to a control algorithm taking account of the detected signal and/or the investigation of the gases is carried out in a controlled manner and according to a control algorithm taking account of the detected signal.

The points in time and sample temperatures at which a gas liberation takes place, which are of particular interest in the context of the invention, can be detected by the continuous detection of the signal in a straightforward manner and in real time.

In order then to obtain, while the thermal analysis is still ongoing, a result of the gas investigation which can be assigned to these points in time and temperatures, the change in the sample temperature can be interrupted, for example for a certain amount of time, and instead the sample temperature can be kept constant when a "liberation process" is detected, in order to investigate the gases liberated at the temperature concerned.

As an alternative to or in addition to taking account of the detected signal only in the temperature regulation, it also comes into consideration, when a "liberation process" is detected, to remove a specific quantity of the liberated gases from the sample relatively quickly and preferably for a short time and to feed the latter to the gas investigation.

In this case, the investigation of the gases is carried out in a controlled manner taking account of the detected signal.

Quite generally, the term "in a controlled manner" in connection with the gas investigation is intended to denote an investigation in which the gases present in the surroundings of the sample are not investigated continuously, but rather the operation of a gas analysis device used for the investigation is actively triggered in some way, including possible active triggering of a transfer of gases from the sample to the gas analysis device.

The control of such a gas transfer can be effected, for example, by an arrangement of one or more valves and/or so-called (gas) injectors disposed upstream of the gas analysis device, also referred to below as a "valve/injection system".

In a particularly preferred embodiment, the gas analysis device comprises a gas chromatograph or a gas chromatograph for separating the different gases with a downstream mass spectrometer (e.g. quadrupole mass spectrometer) for the actual gas analysis.

In an embodiment, a sample chamber containing the sample to be investigated is connected via a transfer line to the gas analysis device. In order to avoid adsorption of transferred gases in the transfer line, the transfer line is constituted so as to be heatable. The same applies to a valve/injection system disposed, as the case may be, at the start, at the end or in the course of the transfer line.

In an embodiment, the valve/injection system comprises an arrangement of a plurality of valves, which can be triggered in a coordinated manner and which make it possible to cause a certain quantity of gas to flow into the valve arrangement at a desired point in time and subsequently, at a desired point in time or over a desired period of time, to discharge the latter again at another point in the direction of the gas analysis device. When a liberation process is detected, a specific quantity of gas can thus be advantageously removed from the sample chamber or the transfer line and then fed to the gas investigation.

As an alternative to or in addition to such a valve arrangement, the valve/injection system can also comprise a so-called (gas) injector. Such injectors are known for example as input components of gas chromatographs. Within the scope of the invention, suitable valve arrangements and injectors are available commercially, for example from the firm JAS ("joint analytical systems").

In order to implement the control algorithm, by means of which the temperature regulation and/or the gas analysis device are controlled, use can advantageously be made of an electronic and in particular a software-based system, i.e. a program-controlled control device (e.g. containing a microcontroller) for example. The signal continuously detected by means of the detection device (and preferably also a signal representative of the current sample temperature) can be fed to such a control system or a control device, in order to generate (calculate) suitable control signals for controlling the temperature regulation or the gas analysis device according to the control algorithm implemented using software running thereon.

The control device used for this can at the same time be the device, or can be structurally combined with the device, that implements a temperature regulation as part of the sample temperature regulation. The control device can also be used, particularly in the case of a software-based design, for an evaluation of the investigation results delivered by the gas analysis device (and also for their correlation with liberation temperatures).

In an embodiment, provision is made such that the control algorithm provides for preliminary processing of the signal detected by the detection device for the continuous ascertainment of a rate of change of this signal.

In an embodiment, the signal is a signal representing the mass of the sample ("mass signal"). If, in this case, a time-related rate of change of this mass signal is continuously formed, a time-related rate of change of the mass is obtained. By monitoring the rate of change of the mass during the controlled change in the sample temperature, it is possible in a straightforward manner to determine a point in time or a temperature at which gases are liberated from the sample, whether it be due to a vaporisation process or a decomposition process. The use of such a process will be noticeable through a marked increase in the absolute value of the (negative) rate of change of the mass.

As a criterion for triggering a "control process", wherein the operation of the temperature regulating device and/or the gas analysis device is influenced, use can thus be made, for example, of the fact that the absolute value of the rate of change of the mass exceeds a specific threshold value which, for example, has previously been set by an operator.

Quite generally, it is advantageous if at least one control parameter of the control algorithm used in the invention can be preset by the operator. The term "control parameter" is intended here to denote a variable entering into the control algorithm as an input variable, which therefore influences the control effected by the control algorithm (in particular the temperature regulation and/or the gas analysis device) and which is established at the latest at the start of the controlled change in the sample temperature. Provision can be made such that such a control parameter is not then changed during the thermoanalysis process.

For example, the control algorithm can take account of the following control parameters, preferably capable of being set in advance: time interval between successive periodic measurements of the sample temperature; time interval between successive periodic detections of the signal or signals; time-related nominal rate of change of the sample temperature in the case of a linear "temperature ramp" according to a temperature program; etc.

In an embodiment, the control algorithm makes provision to trigger a "control event" for the temperature regulation or the gas analysis device on the basis of predetermined (mathematical) criteria being met by the detected signal and/or by an ascertained rate of change of the signal.

Such criteria are also based on one or more control parameters of the control algorithm. If the criterion consists, for example, in that an ascertained rate of change (e.g. the aforementioned rate of change of the mass) exceeds a specific threshold value, this threshold value can be regarded as a control parameter, which can preferably be preset by an operator (just like other control parameters).

Each "control process", which in the course of the controlled change in the sample temperature is always triggered when a predetermined criterion is met, signifies some kind of change in the operation of the temperature regulation and/or of the gas analysis device (compared to the case where no "control process" is triggered).

In an embodiment, provision is made for example such that the control process comprises a change in the sample-temperature rate of change otherwise brought about (without the control process) by the temperature regulating device and/or an operational start-up of the gas analysis device.

Thus, if a sample temperature rising strictly monotonically over the course of time (e.g. with a constant time-related rate of change of the sample temperature) is provided, for example, by a previously set temperature program, the effect of the triggering of the control process can be that, as from this point in time, a rate of change of the sample temperature deviating from the original preselection is brought about, preferably a much smaller rate of change, more preferably even a rate of change of zero (sample temperature is kept constant).

As far as a termination of this "deviating temperature regulation" from the start of the "control process" is concerned, there are in particular to possibilities:

On the one hand, provision can be made such that this particular temperature regulation (e.g. with maintenance of a constant sample temperature) is ended again after a predetermined period of time. This period of time can for example be provided as a presettable parameter. The previously set temperature program can then be continued, for example, at the point (temperature) at which it was interrupted by the control process.

The duration of the interruption of the temperature program can correspond, for example, to the period that is typically required by the gas analysis device to subject a specific quantity of gas to an examination. Such a quantity of gas can be transferred to the gas analysis device, for example as a result of the triggering of the control process.

On the other hand, a termination of the particular temperature regulation can be provided at the point in time at which the examination of liberated gases by the gas analysis device is actually ended, which can be implemented for example by a corresponding check-back indication from the gas analysis device or an evaluation device connected thereto.

As an alternative to or in addition to a change in the operation of the temperature regulating device, a change in the operation of the gas analysis device can take place as a result of the control process. In a preferred embodiment, provision is made for example such that, when the control process is triggered, a specific quantity of gases from the surroundings of the sample is carried away and fed to the gas investigation. This can be implemented for example by corresponding triggering of the valve/injection system already mentioned above. Such triggering of the valve/injection system signifies an "operational start-up of the gas analysis device".

In an embodiment, provision is made such that the control algorithm provides a predefined temperature program with a specific time-dependent change in the temperature of the sample and a temporary interruption of the temperature program at a point in time at which the meeting of predetermined criteria by the detected signal and/or by an ascertained rate of change of the signal is detected.

In a development, provision is made such that the gas analysis device is operated during the interruption of the temperature change and the control algorithm provides for a continuation of the temperature change after completion of a gas investigation by means of the gas analysis device.

In an embodiment, provision is made such that the thermoanalysis device further comprises an evaluation device which, after completion of the controlled change in the temperature of the sample, delivers an evaluation result on the basis of the temperature of the sample thereby measured and a result of the gas investigation, said evaluation result indicating the temperature of a thermal decomposition or evaporation process and preferably also containing an assignment of this temperature to a respective result of the gas investigation. A time- or temperature-resolved analysis of thermal decomposition products, for example, can thus advantageously take place, wherein a direct correlation between decomposition temperature(s) and gas analysis result(s) can also take place in a fully automatic operation.

The thermoanalysis device according to the invention and the thermoanalysis method which can be performed therewith can be used particularly advantageously for characterising substances, in particular technical materials. In contrast with known methods, the informative value and degree of detail of the analysis result is increased considerably.

BRIEF DESCRIPTION OF THE DRAWINGS

The invention is described further below with the aid of an example of embodiment making reference to the appended drawings. In the figures.

DETAILED DESCRIPTION OF THE INVENTION

Figure 1:
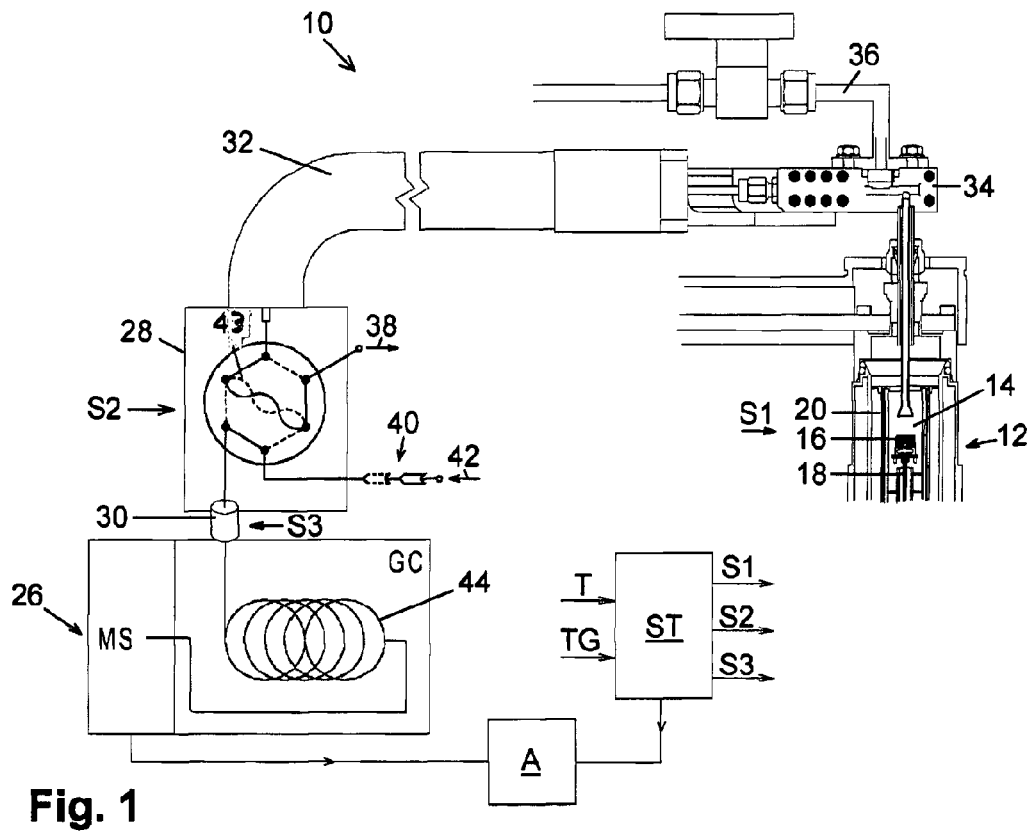
FIG. 1 represents an inventive thermoanalysis device according to an example of embodiment.

FIG. 1 shows a thermoanalysis device 10, comprising a thermogravimetric cell 12 with a sample chamber 14 formed therein, in which a sample 16 is disposed on a sample holder 18.

Electrical heating (e.g. microwave oven) 20 also disposed in sample chamber 14 forms, together with a control unit ST controlling the heating operation and a sensor (not represented) for measuring temperature T of sample 16, a controllable temperature regulating device for the controlled change of sample temperature T in the course of a thermoanalysis.

In the example of embodiment represented, control unit ST is a processor-controlled device, on which a corresponding control algorithm runs software-based, said control algorithm bringing about, amongst other things, the controlled change in sample temperature T, here for example controlled heating-up of sample 16 at a, for example, constant time-related heating-up rate. For this purpose, control unit ST emits a control signal S1 for controlling the heat output of electrical heating 20 and thus regulates the desired heating-up of sample 16 taking account of continuously measured actual sample temperature T.

During the change in sample temperature T in the course of the thermoanalysis, signals can be detected and recorded that are characteristic of different properties of sample 16.

In the example represented, the mass of sample 16, for example, is continuously measured, for which purpose sample holder 18 is connected to a balance (not represented) or contains such a balance. A mass signal TG indicating the current sample mass is delivered by the balance to control unit ST.

The components of device 10 described hitherto form, as such, a thermogravimetric device of the conventional kind. It is thus possible to measure and record temperature-related changes in sample mass TG in a time- and temperature-resolved manner.

Figure 2:
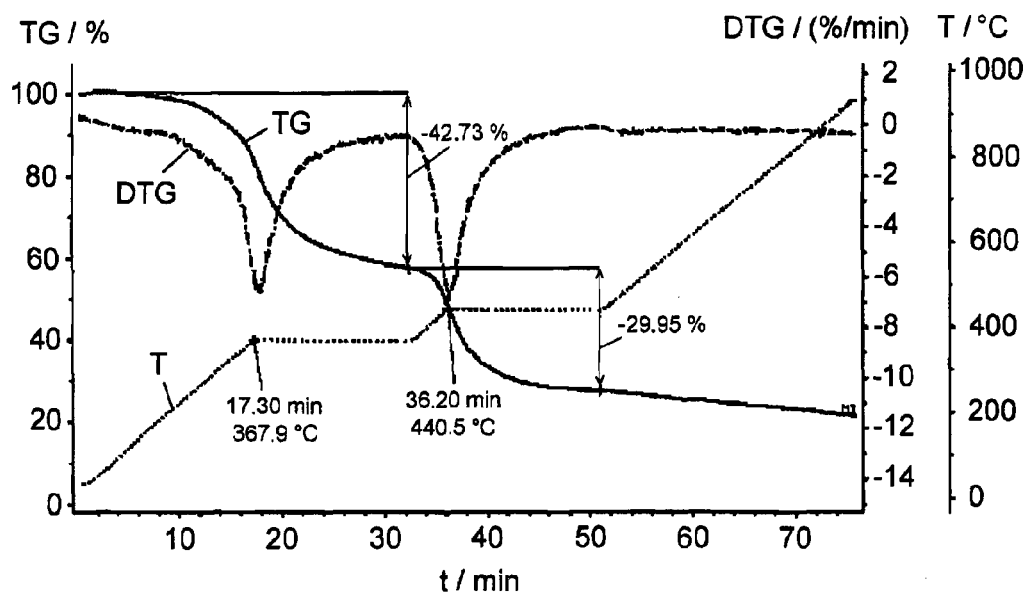
FIG. 2 represents an exemplary time-related course of different variables in a thermoanalysis method carried out with the device of FIG. 1.

FIG. 2 represents, by way of example, the process of a thermogravimetric investigation of a specific rubber mixture by means of device 10 represented in FIG. 1. The dotted line in FIG. 2 shows the course of sample temperature T, and the solid line shows the course of sample mass TG, in each case plotted against time t.

It can be seen from this that, in the course of the heating-up of sample 16, its mass TG diminishes, which in the represented example can be traced back to thermally induced decomposition processes.

In the manner described below, device 10 permits a very informative thermoanalysis, inasmuch as a direct correlation between individual decomposition temperatures or "mass loss stages" and the composition of the volatile components (gases) thereby liberated is thus enabled.

For this purpose, device 10 further comprises a gas analysis device 26, which in the represented example is formed by a gas chromatograph GC with a downstream quadrupole mass spectrometer MS and is coupled with a thermogravimetric cell 12 via a heatable transfer line 32, a controllable valve arrangement 28 and a controllable injector system 30.

Transfer line 32 is connected via an adapter 34 to thermogravimetric cell 12, wherein a bypass line 36 emerges in the region of adapter 34, by means of which bypass line transfer line 32 and downstream components 28, 30 and 26 can be "swept" with helium.

Valve arrangement 28 forms, together with injector system 30, a valve/injection system for gas analysis device 26, said valve/injection system being able to be triggered by control unit ST, wherein helium (or another inert gas) flowing via bypass line 36 serves as a carrier gas for the gases which can thus be fed to gas analysis device 26.

Controllable valve arrangement 28 comprises six valve connections, which are symbolised by six dots in FIG. 1 and which can be connected to one another in different ways via individual valves (not represented), depending on the "switching state". As can be seen from the figure, one of the valve connections is directly connected to the end of transfer line 32. A further valve connection is permanently connected to a vacuum pump (not represented) (an arrow 38 symbolises the removal by suction at this point). A further valve connection is connected via valve 40 to a carrier gas supply connection (an arrow 43 symbolises the carrier gas supply of this point). The carrier gas here is, for example, helium, which is present at valve 40 at a pressure of, for example, several bar. A further valve connection is connected to an inlet of injector system 30.

Valve arrangement 28 is driven into one of two possible switching states via a supplied control signal S2 by the control algorithm running in control unit ST.

In a first switching state, the valve connections are connected to one another in the manner symbolised in the figure by the solid lines between the valve connections, and the carrier gas supply valve 40 is opened. In this first switching state, an investigation of gases originating from sample chamber 14 does not take place. On the contrary, "sweeping with the inert gas (helium)" takes place in this switching state. Helium supplied via bypass line 36 flows through transfer line 32 and further through valve arrangement 28 to the suction connection (see arrow 38). Moreover, helium is supplied via opened valve 40 and is conveyed onward via valve arrangement 28 to injector system 30.

If a "gas liberation process" is detected in the course of the thermoanalysis of sample 16, a "control process" is triggered by control unit ST, said control process effecting a switch-over of valve arrangement 28 into a second switching state via control signal S2.

In this second switching state of valve arrangement 28, its valve connections are connected to one another in the manner symbolised in the figure by the dashed lines between the valve connections. The second switching state serves to supply injector system 30 with a "gas sample" stored in the region of valve arrangement 28, said gas sample having previously been fed from sample chamber 14 via transfer line 32 into valve arrangement 28. The supply of this gas sample is driven, while still in the first switching state, by the helium flowing through transfer line 32. However, when valve arrangement 28 is then brought into the second switching state, a certain quantity of the gases originating from sample 16 is "captured" in a gas sample reservoir 42 of valve arrangement 28 and made available for supplying injector system 30. Carrier gas supply valve 40 is closed in this second switching state.

In a manner known per se, the gas sample is then fed by means of injector system 30 to a capillary ("separation column") 44 of gas chromatograph GC. The individual gases or gas components then arrive at mass spectrometer MS with respective time lags (retention times). Injector system 30 is driven here by control unit ST by means of a control signal S3 in order to introduce the gas sample into capillary 44.

The results of the gas examination(s) carried out during the thermoanalysis by means of gas analysis device 26, i.e. in this case one or more retention time-resolved mass spectra, are brought together in an evaluation device A with the information available or recorded in the region of control unit ST concerning the course of sample temperature T and the other detected signal or signals and are evaluated at least partially automatically by means of evaluation device A.

A distinctive design feature of thermoanalysis device 10 thus already consists in the fact that a gas analysis device (28, 30, 26) constituted so as to be controllable is used in a direct coupling (via transfer line 32) with a device for thermoanalysis (thermogravimetric cell 12).

With regard to the embodiment of control unit ST and the thermoanalytical method implemented therewith, a further distinctive feature of device 10 consists in the fact that, during the controlled change in sample temperature T in the case of the triggering of the "control process", a special triggering/operational change of the temperature regulation of the sample temperature, described in greater detail below, is also carried out.

A control algorithm running in control unit ST comprises preliminary processing of mass signal TG delivered by the thermal balance, said preliminary processing consisting in the fact that a time-related rate of change DTG of the sample mass is continuous ascertained from signal TG (in "real time", e.g. periodically in small time intervals). This mass change signal DTG is also entered in FIG. 2.

The value of change signal DTG is monitored during the thermoanalysis. If the value of signal DTG meets a predetermined criterion, here for example if the absolute value of signal DTG is greater than a previously set threshold value of 5%/min, the "control process" is triggered, the effect of which in the represented example is that the increase in sample temperature T normally provided at a constant heating rate of 20 K/min is automatically interrupted and the previously described gas investigation by means of gas analysis device 26 is initiated (triggering of valve arrangement 28 and injector system 30).

In other words, the temperature regulation of sample 16 as well as the investigation of gases liberated therefrom is controlled in device 10 according to a control algorithm taking account of mass signal TG detected by means of thermogravimetry (after further processing into a mass change signal DTG).

In the course of a thermoanalysis represented by way of example in FIG. 2, such a control process is triggered for the first time after a time t of 17.3 min and a sample temperature T of 368° C. The threshold value for mass change signal DTG relevant for this, in the example −5%/min, has previously been set by the operator as a "control parameter".

As can be seen from FIG. 2, the heating-up of sample 16 is maintained from this point in time t=17.3 min for a specific length of time (in the example, approx. 15 min) and the decomposition gas being liberated at sample 16 is allowed to flow for a short time into valve arrangement 28 or is fed via valve/injection system 28, 30 to gas chromatograph CG with downstream mass spectrometer MS. A measurement of retention time-resolved mass spectra is automatically started.

The control algorithm used here accordingly provides a predefined temperature program with a specific time-dependent change in temperature T of sample 16, which however is always temporarily interrupted when a "control process" is triggered. During such an interruption of the change in sample temperature T, gas analysis device 26 is operated in order to investigate a "gas sample" taken at the time when the control process is triggered.

The temperature change is automatically continued after termination of the operation of gas analysis device 26. In the example of FIG. 2, this takes place at a time t of approx. 32.5 min. From this time, a "normal operation" of electrical heating 20 again takes place to achieve a heating rate of 20 K/min.

In the represented example, a "control process" is then again triggered at a time t of 36.2 min and a temperature of 441° C. This control process in turn produces the same control processes as already described above for the control process lying at t=17.3. A gas investigation by means of gas analysis device 26 is therefore also automatically started at time t=36.2 min and the heating-up of sample 16 is interrupted. After completion of this measurement, the temperature program is continued in thermogravimetric cell 12. In the represented example, this "normal operation" starts again at a time t of 51.0 min.

As can be seen from FIG. 2, no further control process is then triggered in the example until sample temperature T has finally reached its previously set end value (here: approx. 925° C.) at a time t of 74.5 min and the thermogravimetric process is therefore ended.

As a result of the special functional coupling of the thermogravimetry on the one hand and the gas analysis on the other hand, or as a result of the special triggering of the gas chromatography or gas chromatography with downstream mass spectrometry, it is advantageously possible to assign the results of the gas analysis directly to a "temperature stage" without an operator intervention being required for this. In the represented example, the results of the gas investigations (at temperatures T of 368° C. and 441° C.) are automatically assigned to the respective temperature stages by means of evaluation unit A and can thus be delivered to the operator in a very informative form.

Figure 3:
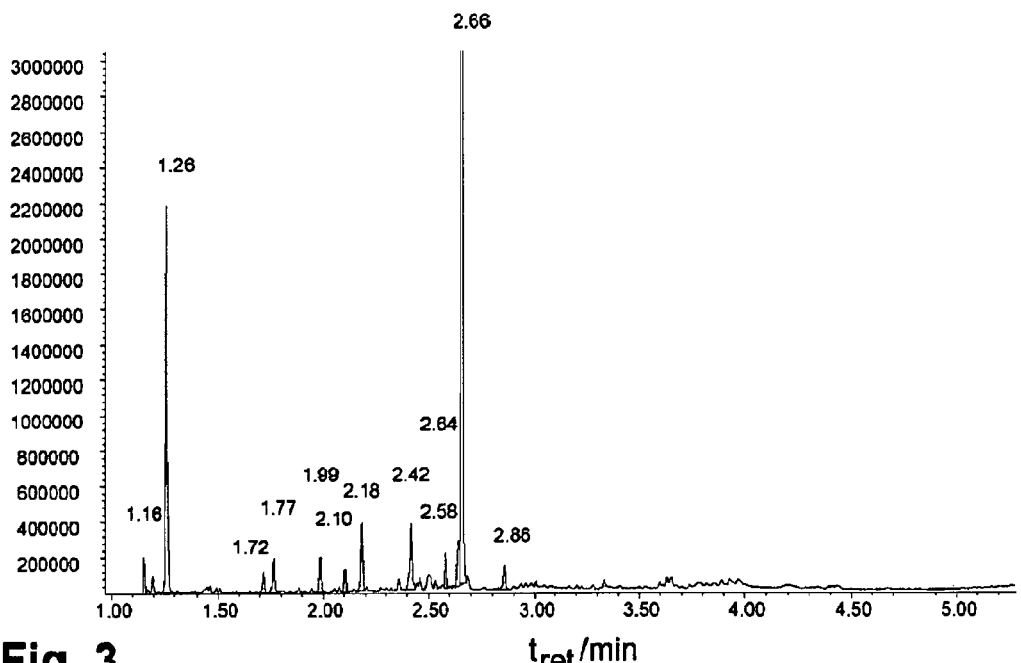
FIG. 3 represents the time-related course of a total mass spectrometer signal recorded in a specific stage of the thermoanalysis method according to FIG. 2.

To illustrate the result of the gas investigation delivered in this example for the "liberation temperature" of 368° C., FIG. 3 shows a total signal of mass spectrometer MS, which has been delivered over the total period of the gas investigation phase starting at t=17.3 min.

In FIG. 3, the counting rate ("abundance") detected by mass spectrometer MS, corresponding to the total ion flow of the mass spectrometer, is plotted as a function of time $t_{ret}$ which has elapsed since the start (t=17.3 min) of the measurement phase. Time $t_{ret}$ corresponds to the preceding gas chromatography retention time of the gas component currently detected by mass spectrometer MS.

The signal peaks in the total mass spectrometer signal shown in FIG. 3 make clear that the gases liberated from sample 16 at respective temperature T of 368° C. comprise a plurality of components.

For the precise identification of these gas components, time-resolved mass spectrograms are detected (and fed to evaluation unit A) over the entire duration of the retention (here: approx. 5 min).

Figure 4:
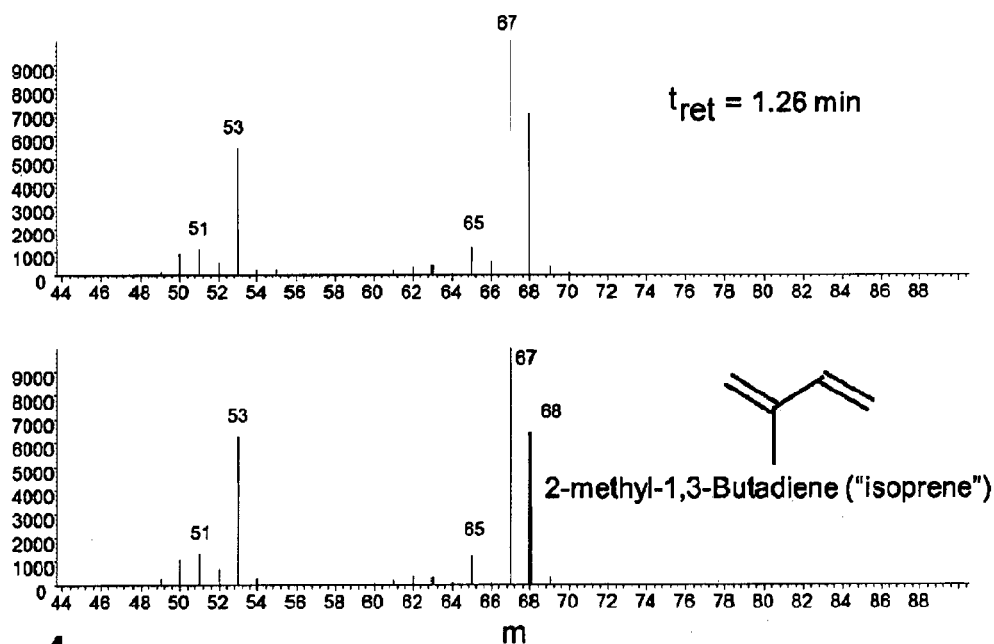
FIG. 4 represents the mass spectrum measured for a specific stage in the mass spectrometry course according to FIG. 3 (top of FIG. 4) and, for comparison, a corresponding spectrum from the literature (bottom of FIG. 4).

FIG. 4 shows in the upper part, by way of example, one such mass spectrum measured with mass spectrometer MS for the peak in the total mass spectrometer signal of FIG. 3 lying at a retention time $t_{ret}$ of 1.26 min. An identification of the gas components concerned can take place in the context of a comparison of such mass spectra with known mass spectra (spectra from the literature), said comparison being carried out partially or fully automatically by evaluation unit A. In the represented example, these components have been identified as methyl butadiene (see spectrum from the literature at bottom of FIG. 4).

What is claimed is:

1. A thermoanalysis device, comprising:
   a controllable temperature regulating device configured to control a change in a temperature of a sample to be investigated;
   a detection device configured to continuously detect at least one signal characteristic of a property of the sample during the change in the temperature; and
   a gas analysis device configured to investigate gases liberated from the sample;
   wherein, during the change in the temperature of the sample, the controllable temperature regulating device is controlled according to a control algorithm taking account of the continuously detected at least one signal characteristic, and the gas analysis device is controlled in a controlled manner according to the control algorithm taking account of the continuously detected at least one signal characteristic;
   wherein the control algorithm provides a predefined temperature program with a specific time-dependent change in the temperature of the sample and a temporary interruption of the predefined temperature program at a point in time at which a meeting of predetermined criteria by the continuously detected at least one signal characteristic and/or by an ascertained rate of change of the continuously detected at least one signal characteristic is detected; and
   wherein, during the temporary interruption of the predefined temperature change program, the gas analysis device is operated and the control algorithm provides for a continuation of the change in the temperature of the sample after completion of a gas investigation by the gas analysis device.

2. The thermoanalysis device of claim 1, wherein a sample chamber containing the sample to be investigated is connected via a heatable transfer line and a heatable valve/injection system to the gas analysis device.

3. The thermoanalysis device of claim 1, wherein the control algorithm provides preliminary processing of the continuously detected at least one signal characteristic for continuous ascertainment of a change rate of the continuously detected at least one signal characteristic.

4. The thermoanalysis device of claim 1, wherein at least one control parameter of the control algorithm is preset by an operator.

5. The thermoanalysis device of claim 1, wherein the control algorithm provides, on a basis of predetermined criteria being met by the continuously detected at least one signal characteristic and/or by an ascertained rate of change of the continuously detected at least one signal characteristic, a control process for the temperature regulating device and the gas analysis device.

6. The thermoanalysis device of claim 5, wherein that the control process comprises a change in a rate of change of the temperature of the sample otherwise brought about by the temperature regulating device and/or an operational start-up of the gas analysis device.

7. The thermoanalysis device of claim 1, further comprising an evaluation device which, after completion of the change in the temperature of the sample, delivers an evaluation result on a basis of the temperature of the sample thereby measured and a result of the gas investigation, said evaluation result indicating a temperature of a thermal decomposition or evaporation process and containing an assignment of this temperature to a respective result of the gas investigation.

8. A method for thermoanalysis, comprising:
regulating a temperature of a sample to be investigated for a controlled change in the temperature of the sample;
continuously detecting at least one signal characteristic of a property of the sample during the controlled change in the temperature of the sample; and
investigating gases which are liberated from the sample;
wherein during the controlled change in the temperature of the sample, the step of regulating the temperature is controlled according to a control algorithm taking account of the continuously detected at least one signal characteristic, and the step of investigating gases is carried out in a controlled manner and according to the control algorithm taking account of the continuously detected at least one signal characteristic;
wherein the method further comprises:
causing a specific time-dependent change in the temperature of the sample;
detecting a point in time at which a meeting of predetermined criteria by the continuously detected at least one signal characteristic and/or by an ascertained rate of change of the continuously detected at least one signal characteristic;
at the point in time, temporarily interrupting the specific time-dependent change in the temperature of the sample; and
during and/or after the step of temporarily interrupting the specific time-dependent change in the temperature of the sample, investigating gases which are liberated from the sample.

9. The method of claim 8, further comprising:
after the step of causing the specific time-dependent change in the temperature of the sample, generating an evaluation result indicating a temperature of a thermal decomposition or evaporation process and assigning the temperature of the thermal decomposition or evaporation process to a result of the step of investigating gases which are liberated from the sample.

10. A thermoanalysis device, comprising:
a controllable temperature regulating device configured to control a change in a temperature of a sample to be investigated;
a detection device configured to continuously detect at least one signal characteristic of a property of the sample during the change in the temperature; and
a gas analysis device configured to investigate gases liberated from the sample;
wherein, during the change in the temperature of the sample, the gas analysis device is controlled in a controlled manner according to a control algorithm taking account of the continuously detected at least one signal characteristic;
wherein the control algorithm provides a predefined temperature program with a specific time-dependent change in the temperature of the sample and a temporary interruption of the predefined temperature program at a point in time at which a meeting of predetermined criteria by the continuously detected at least one signal characteristic and/or by an ascertained rate of change of the continuously detected at least one signal characteristic is detected; and
wherein, during the temporary interruption of the predefined temperature change program, the gas analysis device is operated and the control algorithm provides for a continuation of the change in the temperature of the sample after completion of a gas investigation by means of the gas analysis device.

11. The thermoanalysis device of claim 10, further comprising an evaluation device which, after completion of the change in the temperature of the sample, delivers an evaluation result on a basis of the temperature of the sample thereby measured and a result of the gas investigation, said evaluation result indicating the temperature of a thermal decomposition or evaporation process and containing an assignment of this temperature to a respective result of the gas investigation.

* * * * *